United States Patent
Carrel et al.

(10) Patent No.: US 8,568,359 B2
(45) Date of Patent: Oct. 29, 2013

(54) AUTOINJECTOR

(75) Inventors: Franck Carrel, Le Pont de Claix (FR);
Frederic Perot, Saint Paul de Varces (FR)

(73) Assignee: Becton Dickinson France, Le Pont de Claix (FR)

( * ) Notice: Subject to any disclaimer, the term of this patent is extended or adjusted under 35 U.S.C. 154(b) by 604 days.

(21) Appl. No.: 12/679,706

(22) PCT Filed: Sep. 25, 2008

(86) PCT No.: PCT/IB2008/003160
§ 371 (c)(1),
(2), (4) Date: Jun. 25, 2010

(87) PCT Pub. No.: WO2009/040672
PCT Pub. Date: Apr. 2, 2009

(65) Prior Publication Data
US 2010/0268170 A1    Oct. 21, 2010

(30) Foreign Application Priority Data

Sep. 25, 2007    (WO) .............................. 2007/003972

(51) Int. Cl.
*A61M 37/00* (2006.01)
*A61M 5/20* (2006.01)
*A61M 5/315* (2006.01)

(52) U.S. Cl.
USPC ........... 604/135; 604/131; 604/157; 604/136; 604/192; 604/218; 604/220

(58) Field of Classification Search
USPC .................. 604/130–156, 187, 192, 218, 220
See application file for complete search history.

(56) References Cited

U.S. PATENT DOCUMENTS

| 2005/0101919 | A1 | 5/2005 | Brunnberg |
| 2005/0203466 | A1 | 9/2005 | Hommann et al. |
| 2006/0178630 | A1* | 8/2006 | Bostrom et al. ............... 604/135 |
| 2006/0189938 | A1 | 8/2006 | Hommann et al. |

FOREIGN PATENT DOCUMENTS

| WO | 02/47746 A1 | 6/2002 |
| WO | 2007/036676 A1 | 4/2007 |
| WO | 2007/099044 A1 | 9/2007 |
| WO | 2007/132353 A2 | 11/2007 |

* cited by examiner

Primary Examiner — Nicholas Lucchesi
Assistant Examiner — Leah Stohr
(74) Attorney, Agent, or Firm — Hoffmann & Baron, LLP

(57) ABSTRACT

The invention relates to an autoinjector (1) comprising:
a housing (30, 30a, 30b), a container movable within said housing between an initial position and an insertion position, said movement being prevented when the container is in its passive state, and permitted when the container is in its active state, and
a safety shield (40) movable with respect to said housing between a first position and a second position, said movement placing the container in its active state,
first retaining means (61, 52) for maintaining said container in its passive state,
characterized in that it comprises
first deactivating means (50, 51), capable of rotating with respect to said first retaining means from a first position, in which said first retaining means maintain said container in its passive state, to a second position, in which said first retaining means allow the passage of said container in its active state, said rotation being caused by movement of said safety shield from its first position to its second position under distal pressure exerted on said housing.

18 Claims, 13 Drawing Sheets

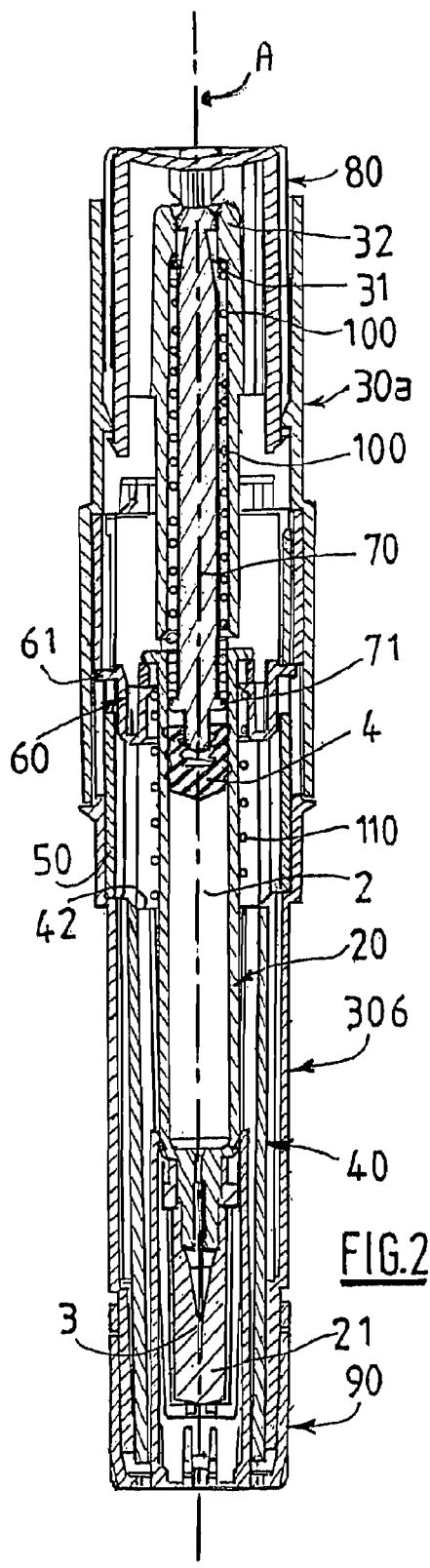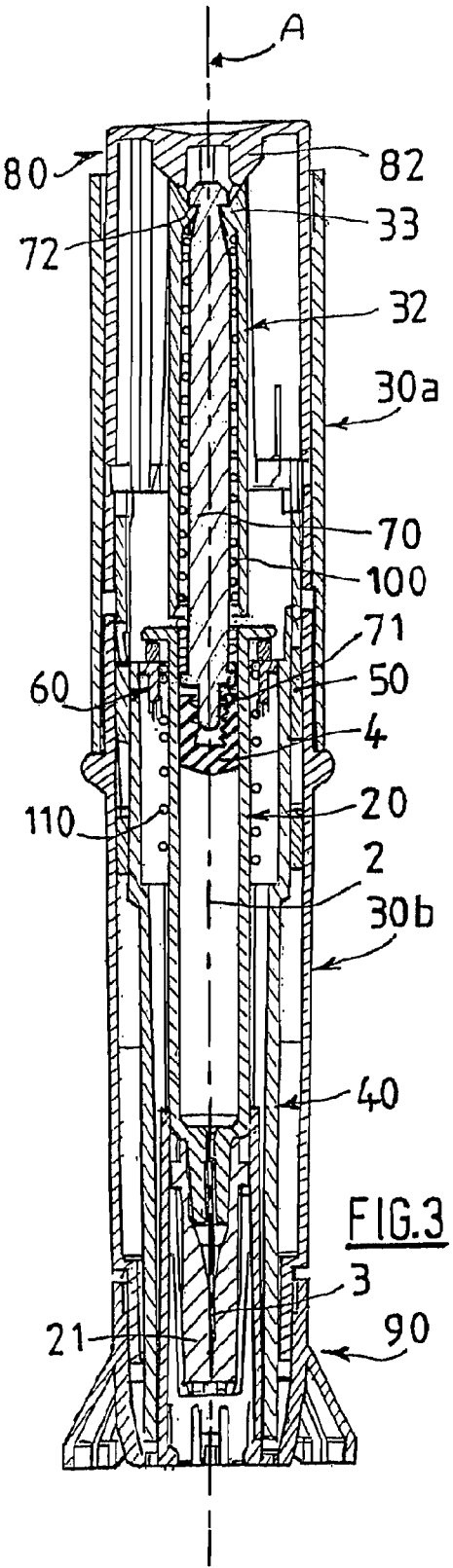

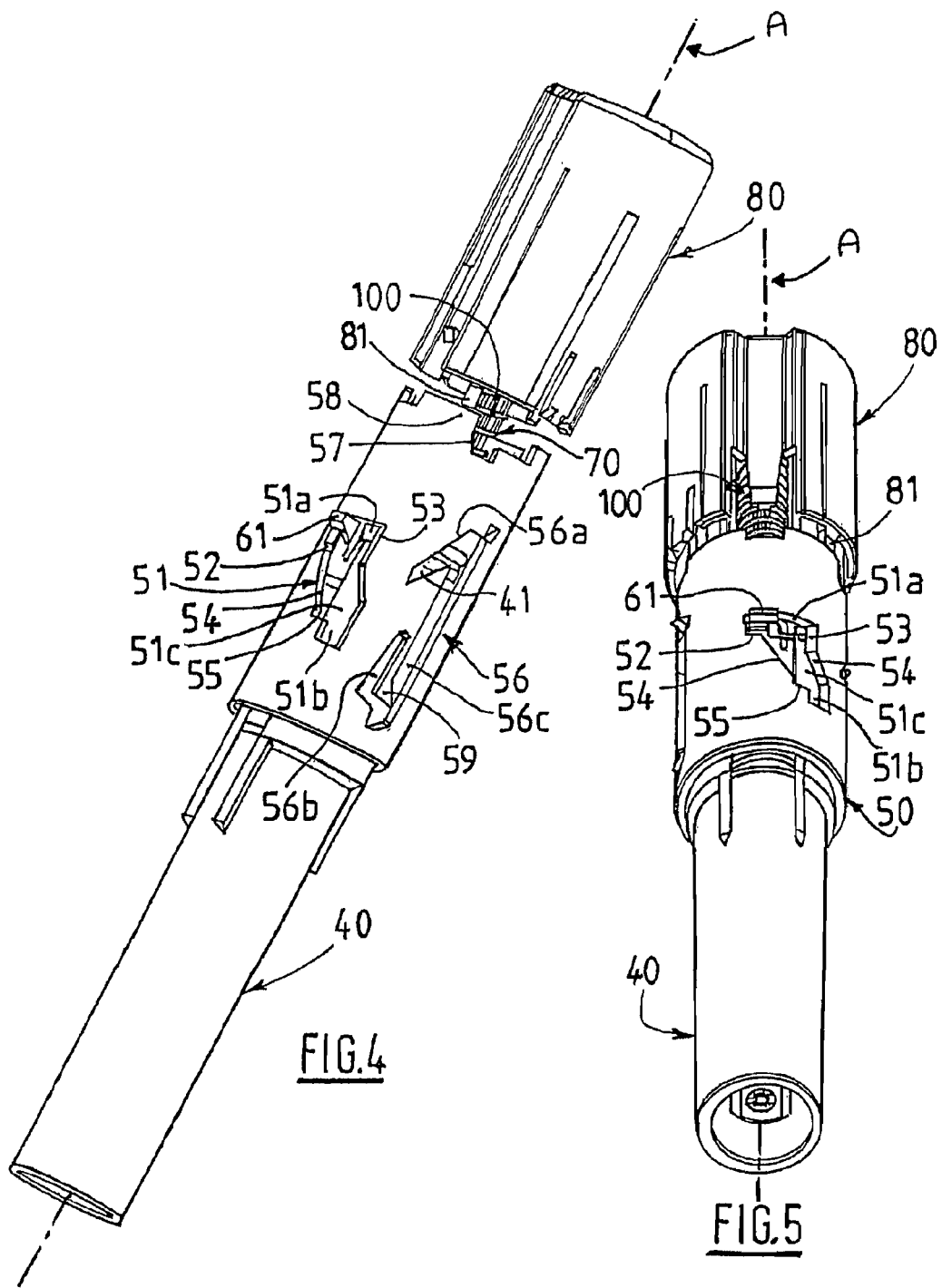

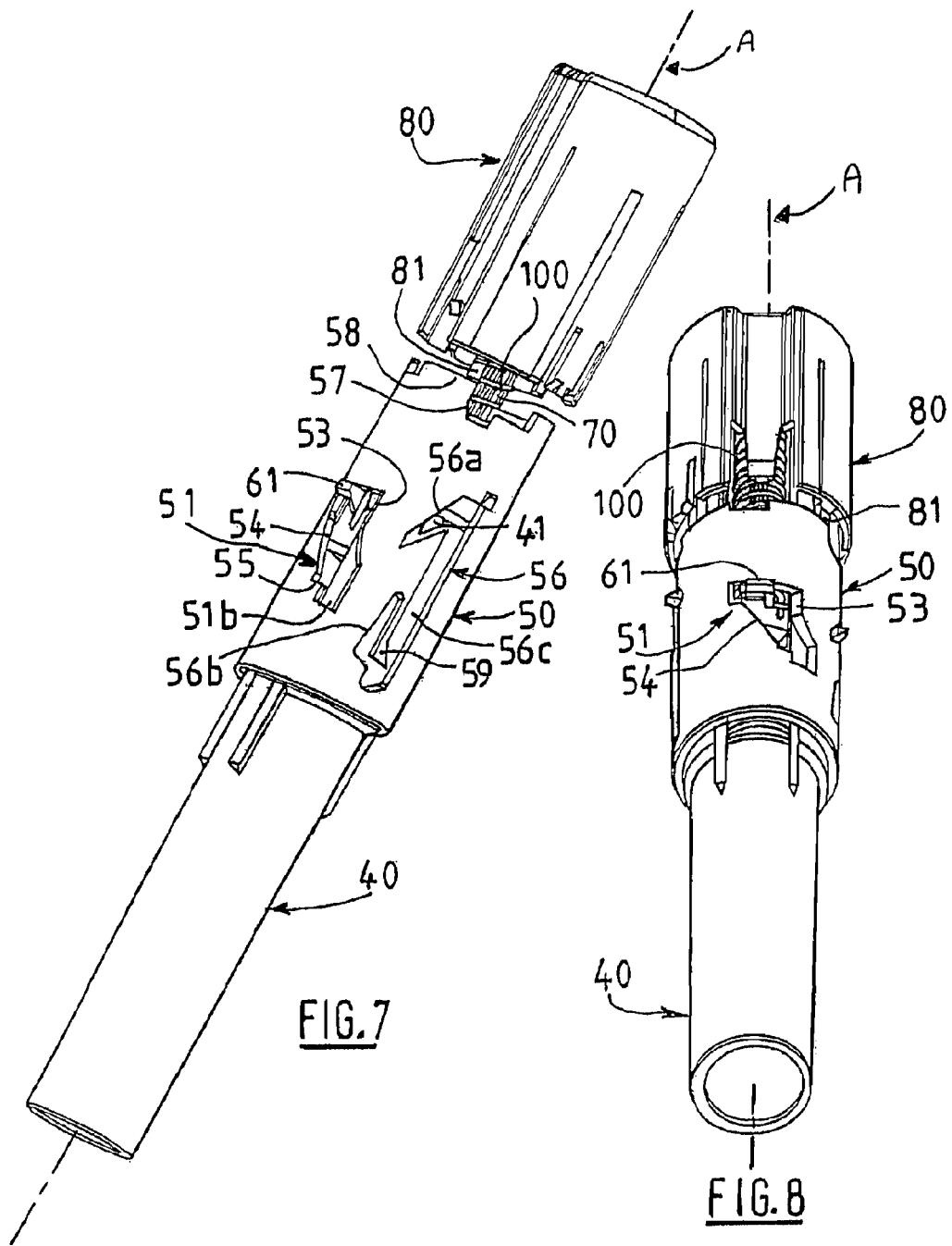

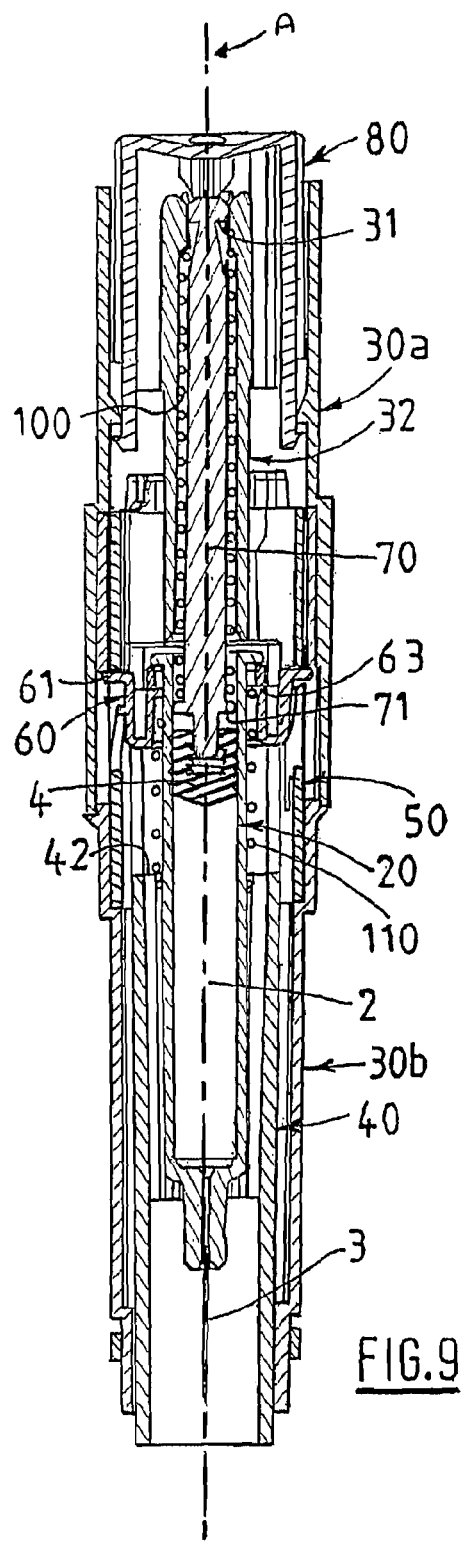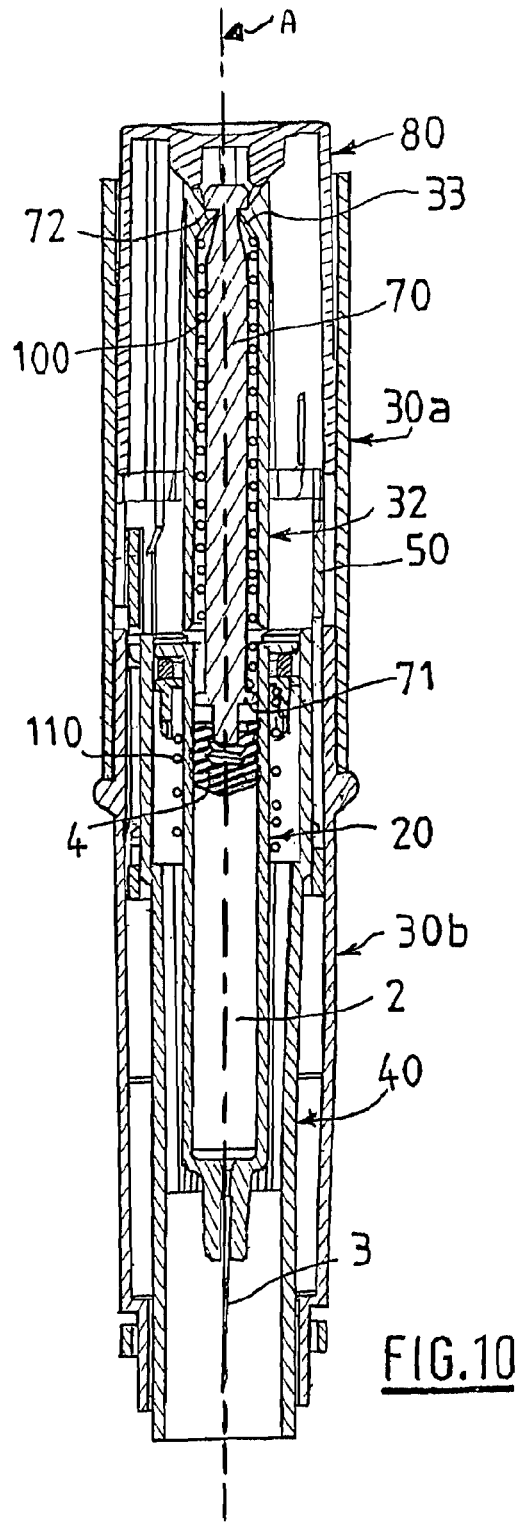

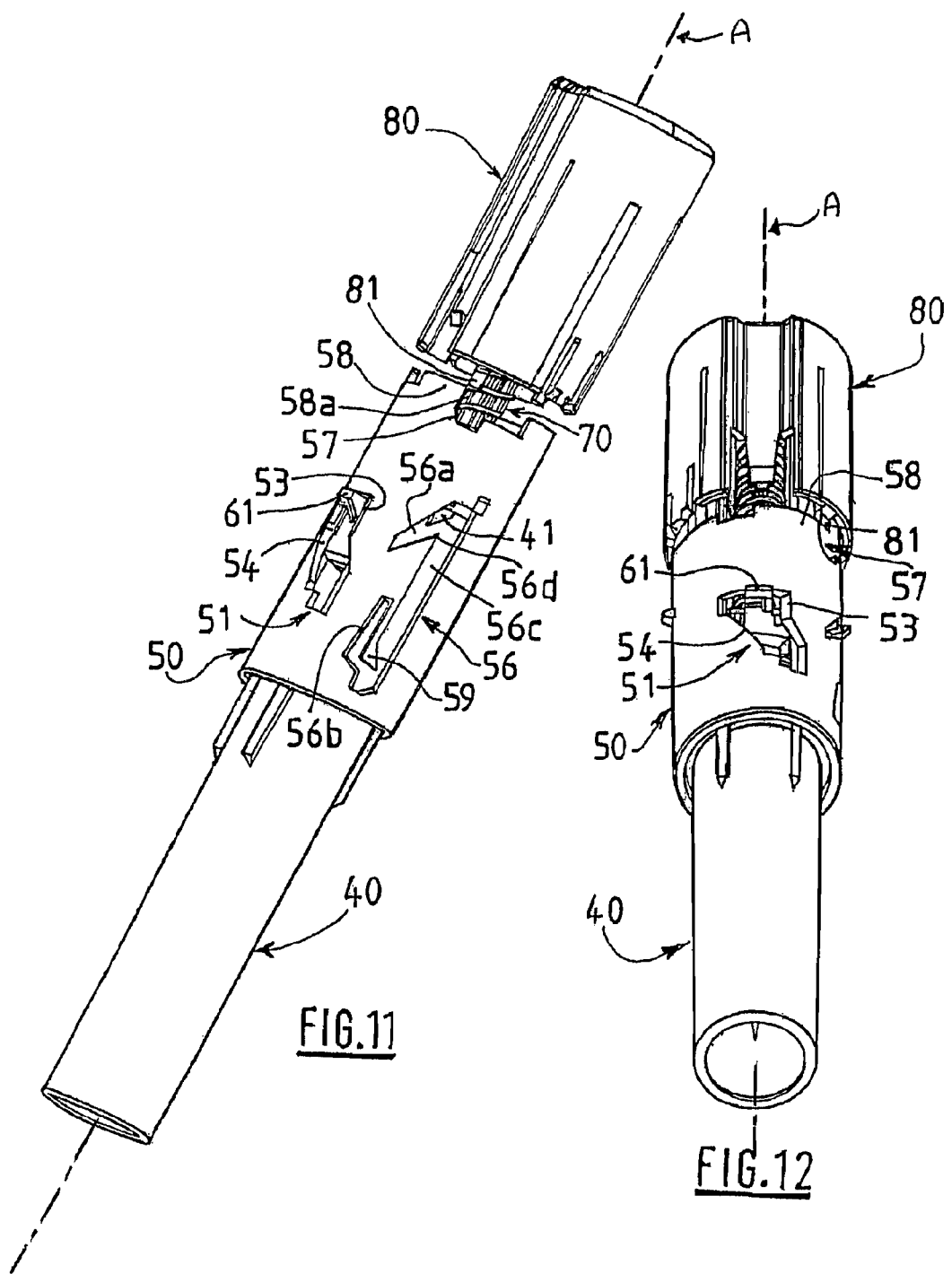

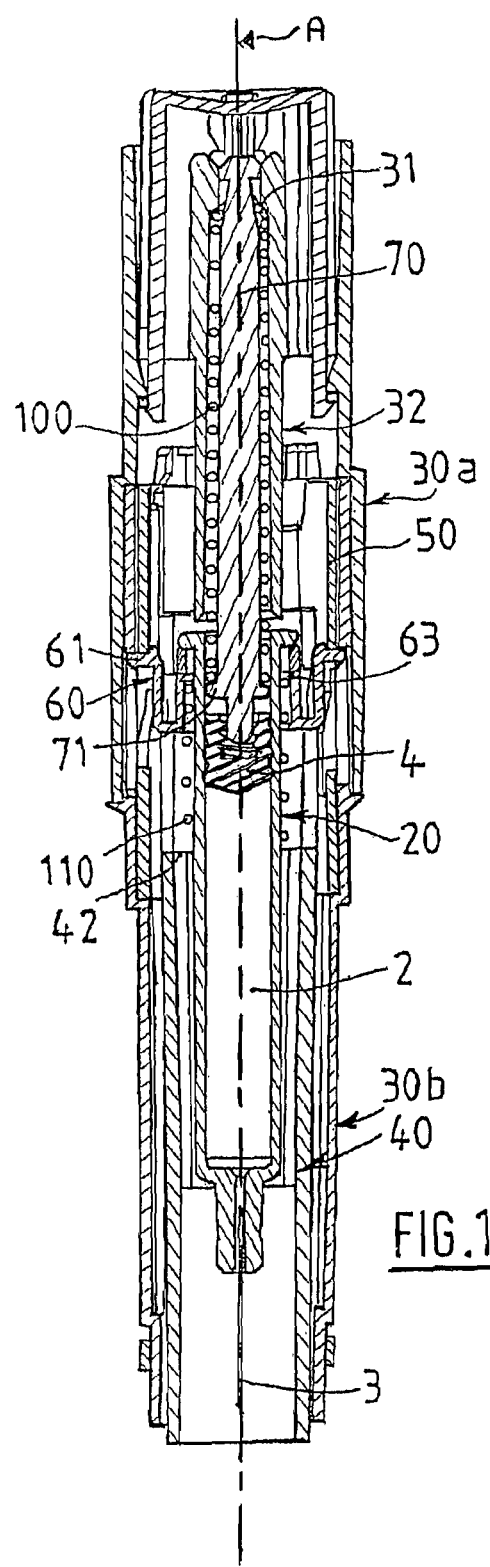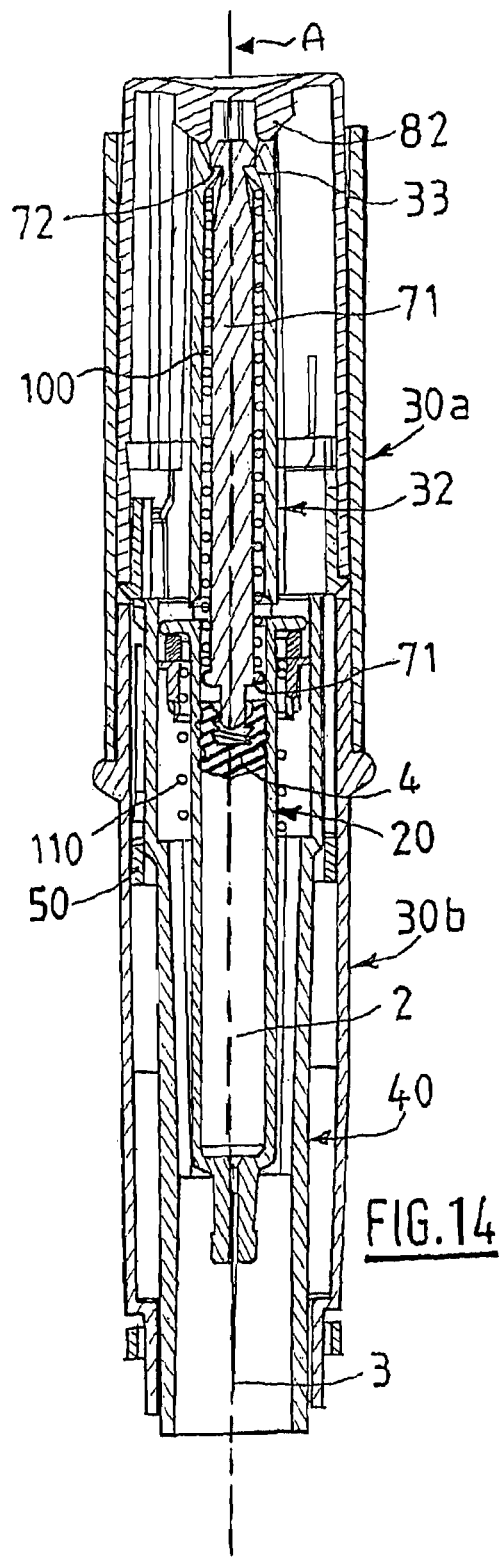

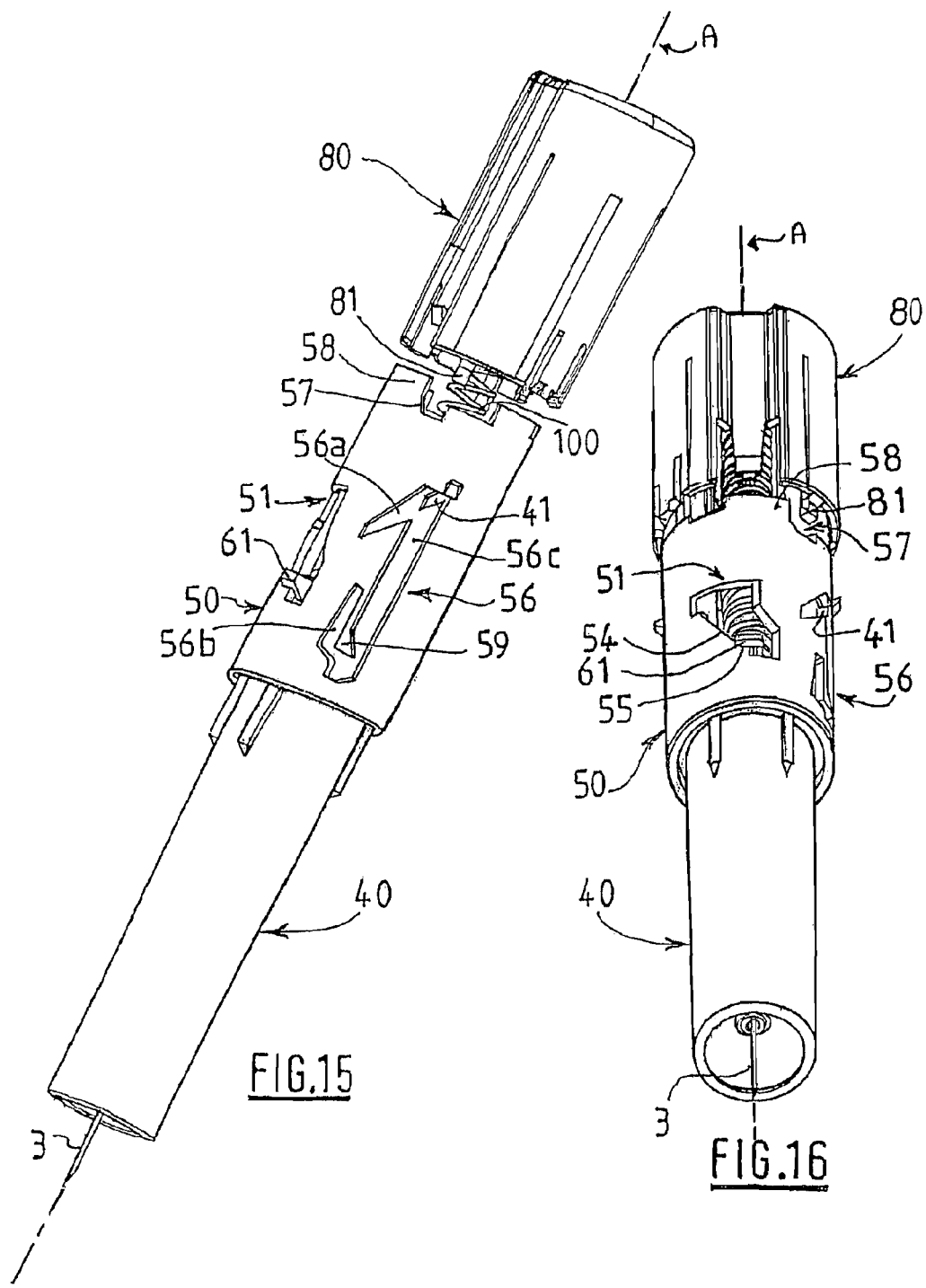

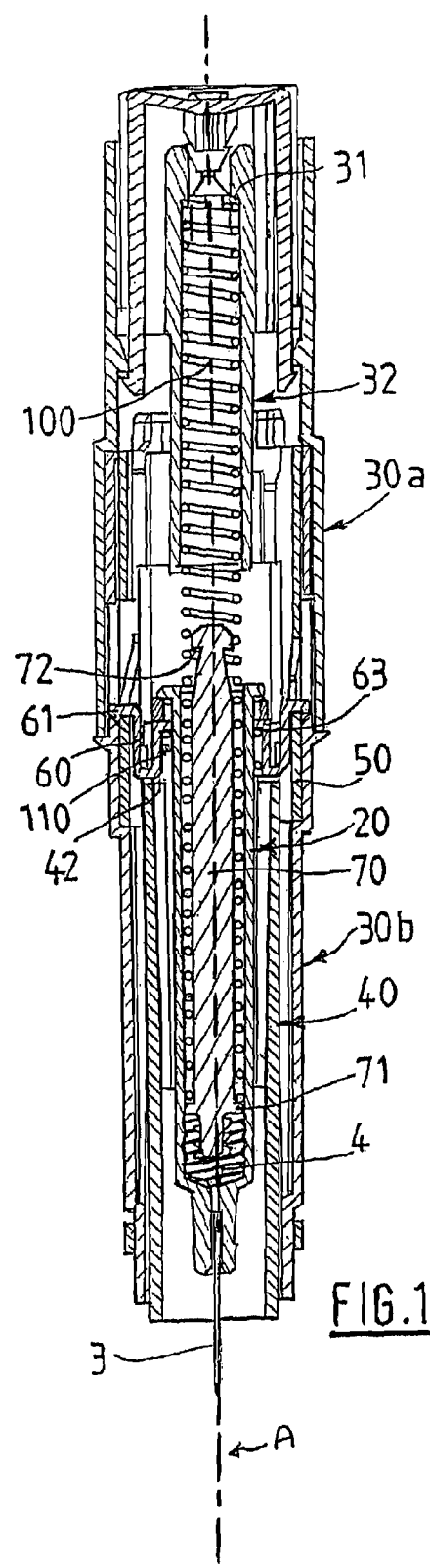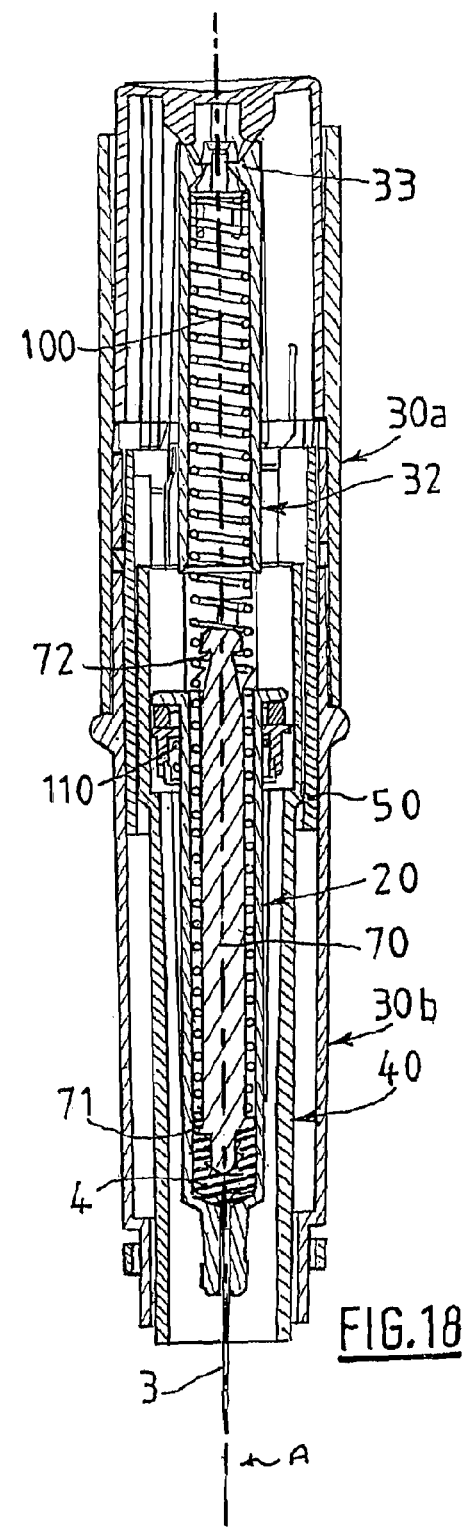

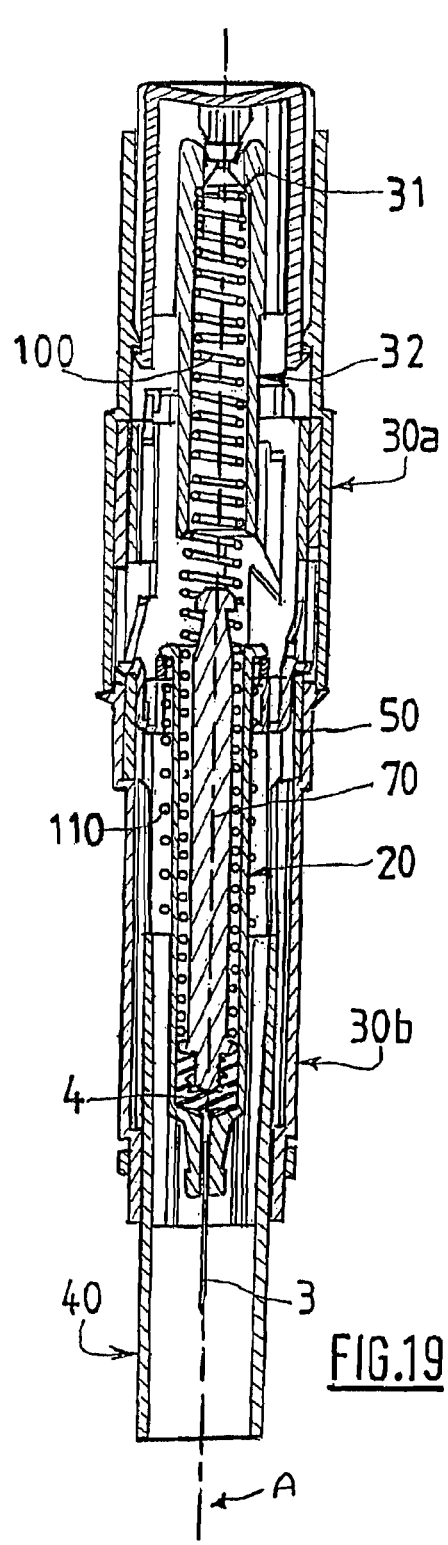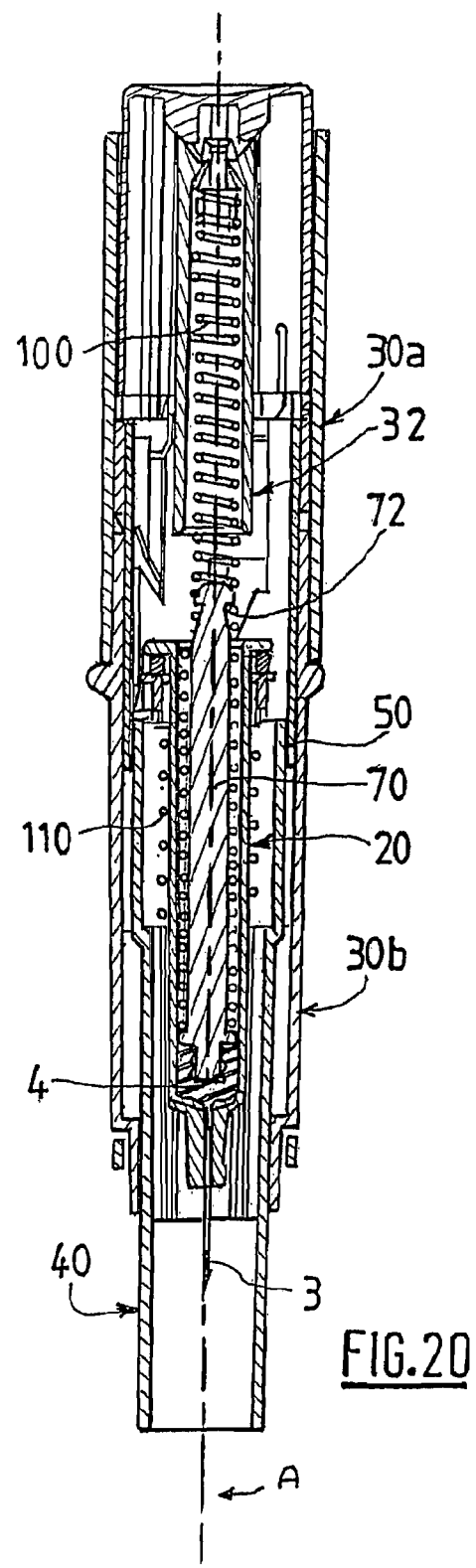

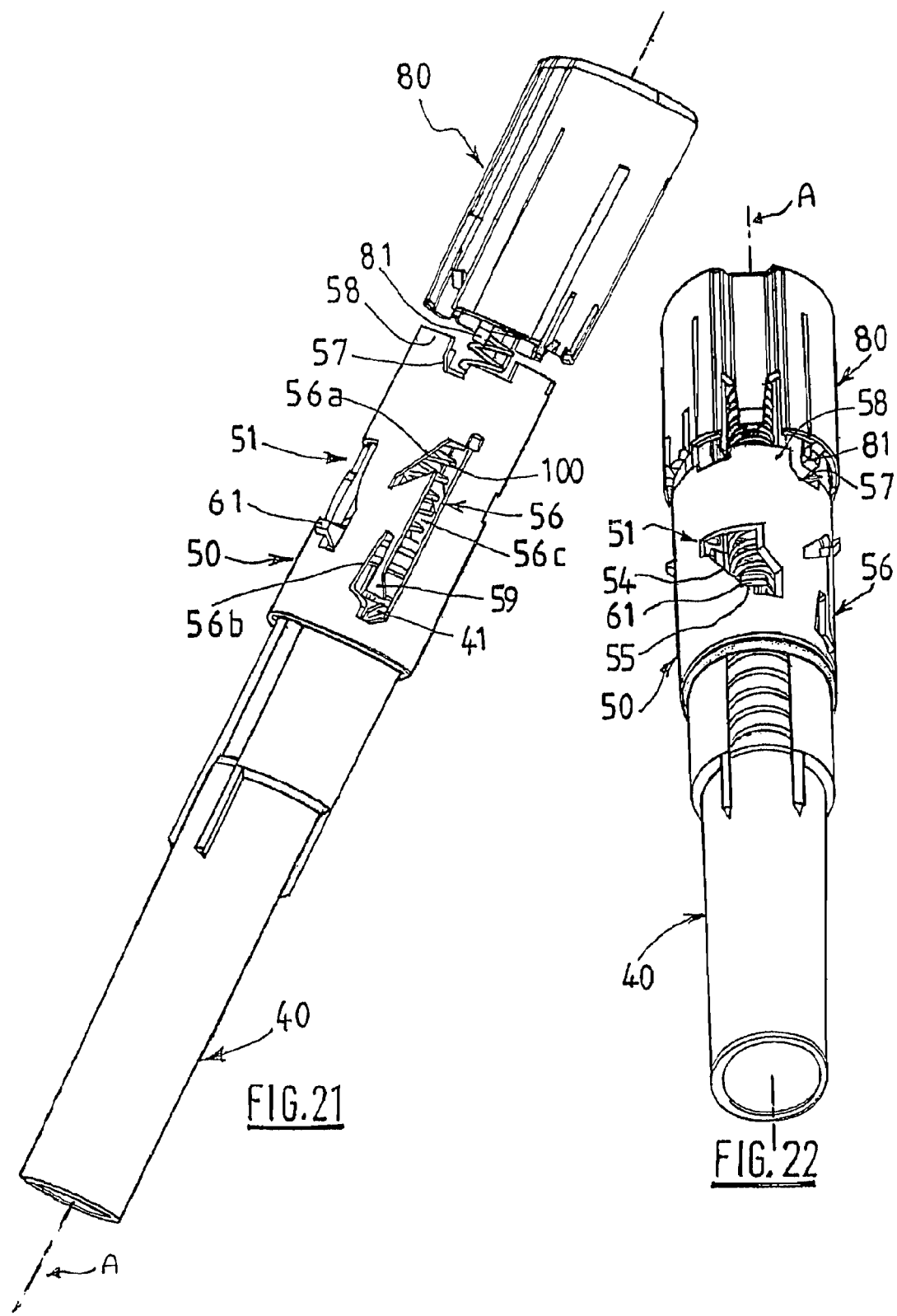

AUTOINJECTOR

Figure 1:
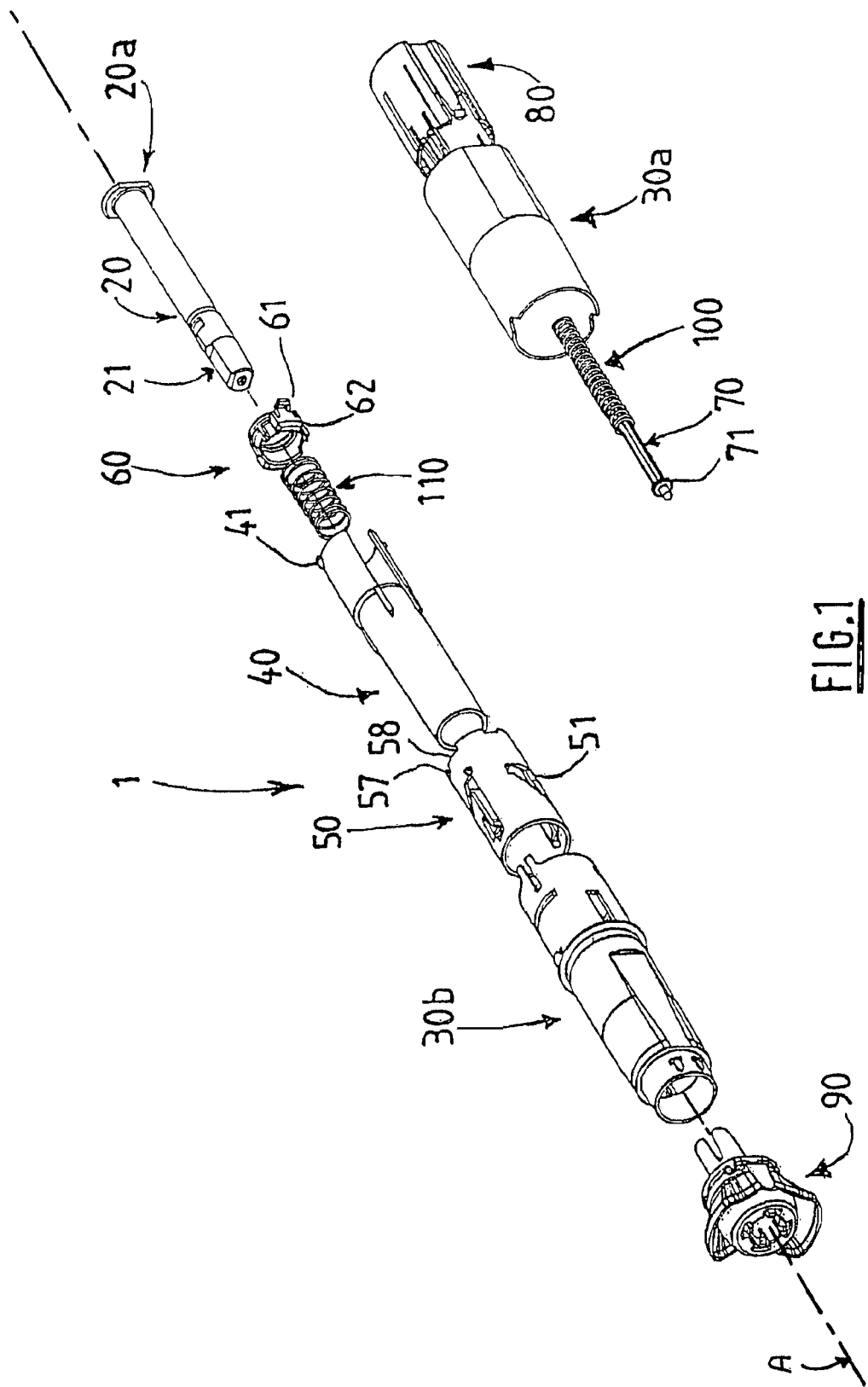

The present invention relates to a device for automatic injection of a medicinal product.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction away from the user's hand, and the "proximal direction" is to be understood as meaning the direction toward the user's hand.

Some illnesses necessitate regular injections of drugs or products, for instance on a daily basis. These injections may be made by the patient, and are thus referred to as self-injections. In order to enable such treatment, self-injection devices have been developed to allow the patient to perform the injection on its own.

Of course, since the patient is usually neither a nurse nor an educated person in medical devices, such self-injectors must prove to be very simple to use and also very safe. In particular, the insertion of the needle must be performed at the right depth, the correct dose of product must be injected, that is to say a complete injection must be performed, and the injector must be deactivated after use before it is disposed of. Preferably, the needle should not be exposed, before and after use, in order to prevent any accidental needlestick injury.

An important requirement of these self-injection devices is that they must not be able to be activated inadvertently, before the patient is ready to perform the injection, and in particular before the device is correctly applied at the right injection site.

Injections devices provided with safety systems preventing the triggering of the insertion of the needle as long as the device is not correctly positioned on the patient's skin have been described. For example, EP 1 349 590 A1 discloses an automatic self-injection device in which the trigger or activation means of the device is locked prior to use, and cannot be unlocked if the user pushes the trigger before the self-injection device is applied to the skin of the patient.

In some cases though, because the operation of self-injecting a product may be stressful for the user and also because it requires that a high force be applied on the skin at the injection site, the user may, inadvertently or not, remove the self-injection device from the skin, after having triggered the insertion of the needle but before the injection has started. If the injection device is provided with a safety system that covers the needle on displacement or removal of the injection device, the injection device is not usable anymore and the medicinal product is lost.

There is therefore a need for an injection device, in particular for automatic injection, that would reduce the force with which the injection device is to be applied on the skin and that would minimize the risks related to a misuse of the injection device by a non educated person in medical devices.

The present invention meets this need by providing a device for automatic injection of a medicinal product into an injection site, said device comprising a safety system that allows a safe and efficient injection, even if the user moves and/or removes the device from the skin once he has triggered the insertion of the needle.

The present invention relates to a device for automatic injection of a product into an injection site, said device having a longitudinal axis A and comprising:

a housing capable of receiving a container, said container being provided at one distal end with a needle and being movable relative to said housing between an initial position, in which a distal end of said needle does not extend beyond a distal end of said housing and in which the container is in one of a passive state and an active state, to an insertion position, distally spaced relative to said initial position, in which said distal end of said needle extends beyond said distal end of said housing, movement of the container out of its initial position being prevented when the container is in its passive state, and being permitted when the container is in its active state, and a safety shield coupled to and movable with respect to said housing between a first position and a second position, proximally spaced with respect to said first position, said safety shield having a free end that is distally spaced beyond a distal end of the needle when said safety shield is on said second position, movement of said safety shield from its first position to its second position placing the container in its active state, first retaining means for maintaining the container in its passive state, said device being characterized in that it comprises first deactivating means, capable of rotating with respect to said first retaining means around said longitudinal axis A from a first position, in which said first retaining means maintain the container in its passive state, to a second position, in which said first retaining means are deactivated and allow the passage of the container in its active state, rotation around said longitudinal axis A of said first deactivating means from its first position to its second position being caused by movement of said safety shield from its first position to its second position under distal pressure exerted on said housing.

The device of the invention is very simple to use. Moreover, as will appear more clearly from the description below, the device of the invention allows a complete and safe injection even if the user mis uses the device and performs mistakes during the use of the device. In particular, in case the user mis-uses the device of the invention, then the product is not lost and the injection may be correctly and safely completed in the end.

In an embodiment of the invention, the device further comprises:

first biasing means coupled to said housing for biasing the container toward said insertion position, said first biasing means being in one of a compressed condition, in which the container is in its initial position, and an extended condition, in which the container is in its insertion position, and second retaining means for maintaining said first biasing means in its compressed condition, triggering means being activatable by application of a force on said triggering means to release said second retaining means, said triggering means being in one of a passive state, in which application of said force on said triggering means cannot cause the release of said second retaining means, and an active state in which application of said force on said triggering means causes the release of said second retaining means, wherein movement of said safety shield from its first position to its second position causes passage of said triggering means from its passive state to its active state.

In an embodiment of the invention, the device further comprises:

third retaining means for maintaining said triggering means in its passive state, second deactivating means, capable of rotating with respect to said third retaining means around said longitudinal axis A from a blocked position, in which said third retaining means maintain said triggering means in its passive state, to a free position, in which said third retaining means allow the passage of said triggering means in its active state, rotation around said longitudinal axis A of said second deactivating means from its blocked position to its free position being caused by movement of said safety shield from its first position to its second position.

In an embodiment of the invention, part of said first and second deactivating means are formed on at least one intermediate sleeve received within said housing, said intermediate sleeve being movable in rotation around said longitudinal axis A from a first position to a second position in response to movement of said safety shield at least out of its first position.

In an embodiment of the invention, said first retaining means comprising at least a ring received within said safety shield and coupled to said container, said ring comprising at least an outer radial stop, said first deactivating means comprises a window arranged in said intermediate sleeve, said window comprising an abutment surface, said radial stop being engaged on said abutment surface in the first position of said intermediate sleeve, and being disengaged from said abutment surface after rotation of said intermediate sleeve around said longitudinal axis A.

In an embodiment of the invention, said third retaining means comprising at least a distal leg located on said triggering means in regard of the proximal end of said intermediate sleeve, said second deactivating means comprise a proximal recess arranged at the proximal end of said intermediate sleeve, said distal leg being in spaced relation to the proximal end of said intermediate sleeve in the first position of said intermediate sleeve, and being in regard with said recess after rotation around said longitudinal axis A of the intermediate sleeve, thereby allowing distal movement of said triggering means by application of a force exerted on said triggering means.

In an embodiment of the invention, the device further comprises guiding means designed for causing the rotation around said longitudinal axis A of said intermediate sleeve with respect to said safety shield when distal pressure is exerted on said housing.

In an embodiment of the invention, said guiding means include at least a peg located on said intermediate sleeve or on said safety shield and a first cam located respectively on said safety shield or on said intermediate sleeve and in which said peg is engaged so as to be able to move slidingly and reversibly within said first cam, said first cam being inclined with respect to the longitudinal axis A of said device, the movement of said peg within said first cam when distal pressure is applied on said housing causing rotation of said intermediate sleeve around said longitudinal axis A.

In an embodiment of the invention, the device comprises first return means designed for biasing said safety shield from its second position to its first position when distal pressure exerted on said housing is released before activation of said triggering means, said guiding means causing the intermediate sleeve to rotate back in its first position around said longitudinal axis A.

In an embodiment of the invention, said first return means comprise at least a spring, said spring being in a compressed condition when said safety shield is in its second position.

In an embodiment of the invention, said first return means further comprise a flexible tab located on said intermediate sleeve, said flexible tab being in a rest position when said intermediate sleeve is in its first position and being in a tangentially deflected position when said intermediate sleeve is in its second position, said intermediate sleeve being movable in rotation around said longitudinal axis A with respect to said housing, said flexible tab having a radial protrusion engaged in a window located on said housing, said flexible tab aiming at coming back to its rest position when distal pressure exerted on said housing is released, thereby causing said intermediate sleeve to rotate back to its first position around said longitudinal axis A.

In an embodiment of the invention, the device further comprises locking means designed for preventing the intermediate sleeve to rotate back around said longitudinal axis A to its first position when distal pressure exerted on said housing is released after activation of said triggering means but before the container reaches its insertion position, said locking means comprising a lateral wall of said recess, said distal leg being at least in abutment on said lateral wall after activation of said triggering means, thereby preventing the rotation around said longitudinal axis A of said intermediate sleeve with respect to said triggering means.

In an embodiment of the invention, said distal leg comprises at least one tooth and said lateral wall comprises at least one groove, said at least one tooth being caused to engage said at least one groove if distal pressure exerted on said housing is released after activation of said triggering means and before the container reaches its insertion position, so that further activation of said triggering means is prevented.

In an embodiment of the invention, said safety shield being movable with respect to the container to a third position, in which the tip of the needle extends beyond a distal end of said safety shield, and to a fourth position, in which the tip of the needle does not extend beyond a distal end of said safety shield, said device further comprises second biasing means coupled to said safety shield for biasing said safety shield from its third position to its fourth position when distal pressure exerted on said housing is released, first arresting means designed for maintaining said safety shield substantially in its third position, if distal pressure exerted on said housing is released after activation of said triggering means and before the container reaches its insertion position, third deactivating means designed for deactivating said first arresting means when the container is in its insertion position.

In an embodiment of the invention, said first arresting means comprise an abutment surface formed in said first cam, said peg coming in abutment on said abutment surface and thereby preventing further movement of said safety shield with respect to said intermediate sleeve when distal pressure exerted on said housing is released after activation of said triggering means and before the container reaches its insertion position.

In an embodiment of the invention, said ring being coupled to the container, said third deactivating means comprise an inclined slope located in said window, said radial stop of said ring cooperating with said slope so as to cause a further rotation around said longitudinal axis A of said intermediate sleeve with respect to said safety shield, when the container moves from its initial position to its insertion position, thereby causing said peg to disengage from said abutment surface and to engage the proximal end of a second cam formed on said intermediate sleeve or on said safety shield, said second cam extending longitudinally in the distal direction.

In an embodiment of the invention, the device further comprises second arresting means for preventing the movement of said safety shield from its fourth position to its third position.

In an embodiment of the invention, said second arresting means comprise a flexible tab located in the distal region of said second cam, said flexible tab being able to be overcome by said peg during the movement of said safety shield from its third position to its fourth position, said flexible tab forming a stop with respect to the proximal movement of said peg when said safety shield is in its fourth position.

In an embodiment of the invention, said first deactivating means is capable of rotating around said longitudinal axis A from its second position to its first position, said rotation being caused by movement of said safety shield from its second position to its first position prior to activation of the triggering means.

Figure 6:
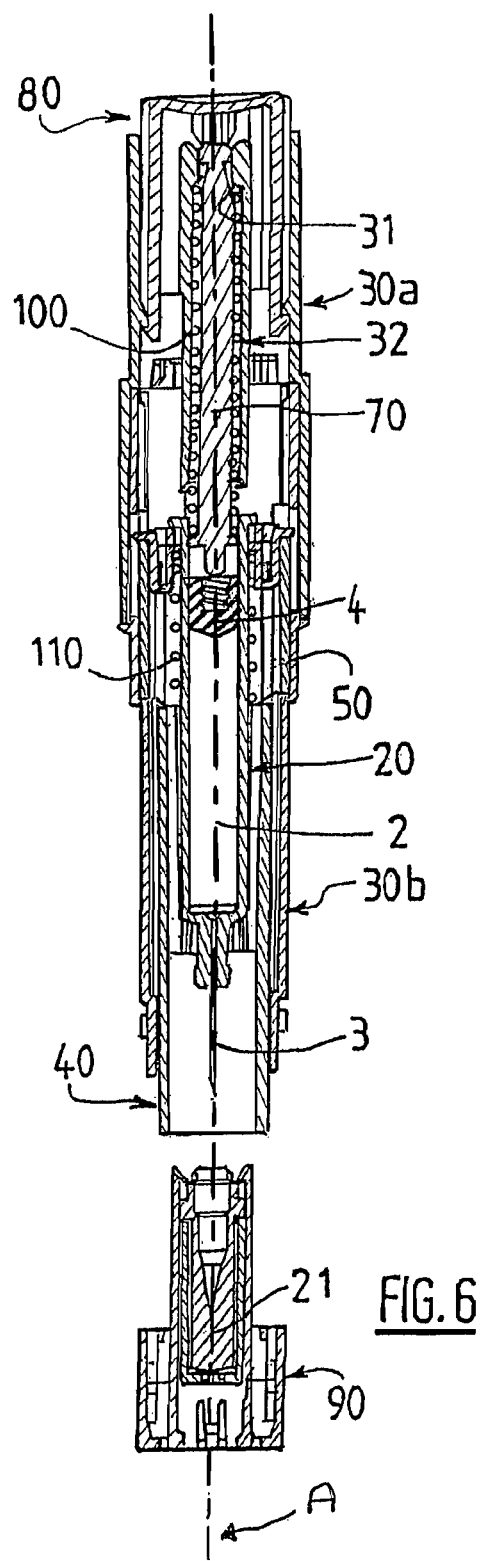
Figure 23:
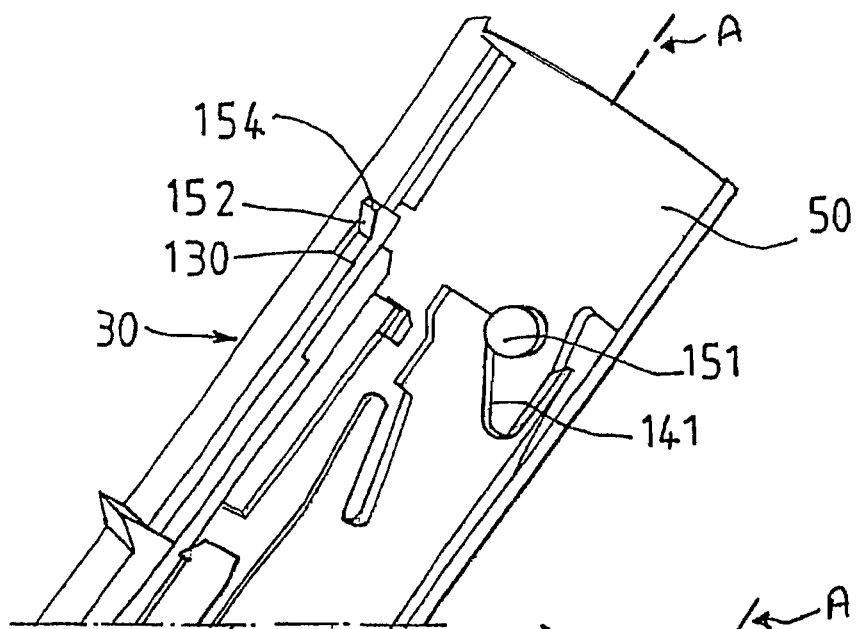
Figure 24:
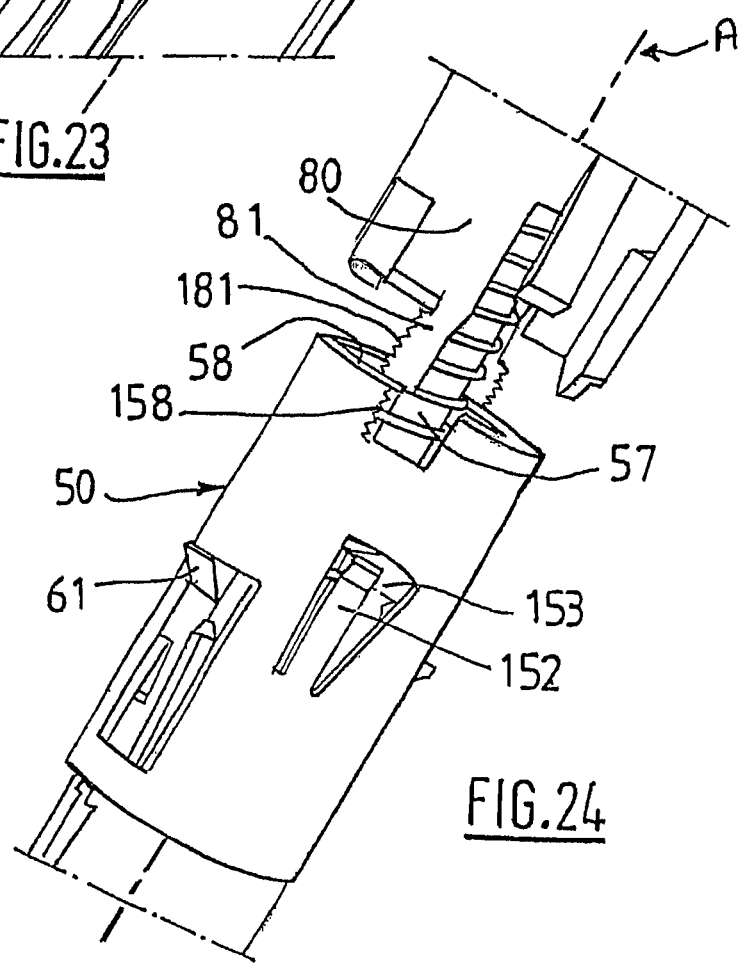

The invention and its advantages will appear more clearly in the light of the following description and the annexed drawing in which:

FIG. 1 is an exploded perspective view of a device according to the invention,

FIG. 2 is a cross section view of the device of FIG. 1 in a ready to use position, FIG. 3 is a cross section view, taken after a rotation of 90° of the device of FIG. 2, FIGS. 4 and 5 are perspective views of the device of FIGS. 2 and 3 with the housing taken out, FIG. 6 is a cross section view of the device of FIG. 1 after removal of the needle shield, FIGS. 7 and 8 are perspective views of the device of FIG. 1 after deactivation of the first retaining means with the housing taken out, FIG. 9 is a cross section view corresponding to the device of FIG. 2 after deactivation of the first retaining means and triggering means in an active state, FIG. 10 is a cross section view, taken after a rotation of 90° of the device of FIG. 9, FIGS. 11 and 12 are perspective views of the device of FIGS. 9 and 10 with the housing taken out, FIG. 13 is a cross section view corresponding to the device of FIG. 2 after the safety shield has reached the end of its stroke, FIG. 14 is a cross section view, taken after a rotation of 90° of the device of FIG. 13, FIGS. 15 and 16 are perspective views of the device of FIG. 1 during the injection with the housing taken out, FIG. 17 is a cross section view corresponding to the device of FIG. 2 at the end of injection, FIG. 18 is a cross section view, taken after a rotation of 90° of the device of FIG. 17, FIG. 19 is a cross section view corresponding to the device of FIG. 2 once the safety shield has been activated, FIG. 20 is a cross section view, taken after a rotation of 90° of the device of FIG. 19, FIGS. 21 and 22 are perspective views of the device of FIG. 1 once the safety shield has been activated with the housing taken out, FIG. 23 is a partial perspective view of the safety shield and the intermediate sleeve of a variant of the device of the invention, FIG. 24 is a partial perspective view of the intermediate shield and the triggering means of the device of FIG. 23.

Referring now to the drawings, on FIG. 1 is shown a device 1 for automatic injection of a product. The device 1 has a longitudinal axis A.

The device 1 comprises a container 20 having an open proximal end 20a and a substantially closed distal end, covered on FIG. 1 by a needle cap 21 in view of protecting the needle 3 (not shown on FIG. 1 but shown on FIGS. 2 and 3) provided at said distal end.

The device 1 further comprises a housing 30 comprising a top body 30a and a bottom body 30b, said top and bottom bodies being coupled together, for example by snap-fit means, after assembly of the device as shown on FIG. 2. As will appear hereinbelow, the housing 30 is intended to receive the container 20, said container 20 being movable relative to the housing 30 between an initial position (shown on FIGS. 2 and 9) in which the distal tip of the needle 3 does not extend beyond the distal end of the housing 30 to an insertion position (shown on FIGS. 15-18) in which the distal end of the needle 3 extends beyond the distal of the housing 30.

As appears more clearly from FIGS. 2 and 3, the top body 30a comprises an inner cylinder 32 provided with a radial rim 31 and with flexible legs 33.

The device 1 further comprises a safety shield 40: the safety shield 40 is received within the housing 30 and is movable with respect to said housing 30 as will appear later. The safety shield 40 is provided with a peg 41 located on the outer wall of the safety shield at the proximal end of said shield. The function of this peg 41 will be explained later.

The device 1 also comprises an intermediate sleeve 50 received between the housing 30 and the safety shield 40. The intermediate sleeve 50 is coupled to the housing 30, for example by snap-fit means not shown. As appears on FIG. 1, the intermediate sleeve 50 is provided with a window 51 cut within its wall: as can be seen more clearly on FIGS. 4 and 5, the window 51 comprises a proximal region 51a, a distal region 51b and an intermediate region 51c linking said proximal and distal regions 51a and 51b, said proximal and distal regions 51a and 51b being tangentially spaced from one another. The proximal region 51a of the window 51 comprises an abutment surface 52 and a rotational stop 53. The intermediate region 51c of the window 51 is delimited by two inclined slopes 54. The intermediate region 51c also comprises an abutment surface 55.

The intermediate sleeve 50 further comprises a cam 56 cut in its wall, said cam 56 being tangentially spaced from the window 51. The cam 56 is better seen on FIG. 4. It comprises a first portion which is an inclined proximal portion 56a, a distal portion 56b and an intermediate portion 56c bridging said proximal and distal portions 56a and 56b together. The junction between the proximal portion 56a and the intermediate portion 56c forms an elbow 56d defining an abutment surface. The intermediate portion 56c is provided in its distal region with a flexible tab 59 reducing the width of said intermediate portion 56c at this point.

The intermediate sleeve 50 is provided at its proximal end with two diametrically opposed recesses 57 and with two diametrically opposed proximal projections 58, adjacent said recesses 57.

The device 1 further comprises a ring 60 received between the safety shield 40 and the intermediate sleeve 50. The ring 60 is coupled to the container 50: on the example shown, it is snap fit on a proximal flange of the container 50. The ring 60 comprises two radial stops 61 extending outwardly. The ring 60 is also provided with two legs 62 extending distally.

The device 1 comprises a piston rod 70 and a push button 80. As shown on FIGS. 2 and 3, the piston rod 70 is provided at its distal end with an outer rim 71 and at its proximal end with an abutment rim 72. The push button 80 is provided with two distal legs 81. The push button 80 is also provided with two inner legs 82 visible on FIG. 3. As will appear later in the description, the push button 80 acts as triggering means of the device 1.

At its distal end, the device 1 is further provided with a deshielder 90 intended to cover and to be coupled to the needle shield 21 before use.

The device 1 is further provided with two helical springs. A first helical spring 100 is received between the piston rod 70 and the push button 80. A second helical spring 110 is received between the container 50 and the safety shield 40.

The operation of the device 1 according to the invention will now be described in reference to FIGS. 2 to 22.

The device is provided to the user in the before use position shown on FIGS. 2-5. The deshielder 90 is not shown on FIGS. 4 and 5.

With reference to FIGS. 2 to 5, the container 20 is in its initial position: the distal end of the container 20 is provided with a needle 3. The tip of the needle 3 does not extend beyond the distal end of the bottom body 30b of the housing 30. On these figures, the container 20 is in its passive state: movement of said container 20 out of its initial position is prevented by means of the radial stops 61 of the ring 60 being in abutment on the abutment surface 52 of the intermediate sleeve 50, as shown on FIGS. 4 and 5. The radial stops 61 of the ring 60 together with the abutment surface 52 act as first retaining means for maintaining the container 20 in its passive state.

On FIGS. 2 and 3 the proximal end of the first spring 100 bears on a radial rim 31 located on an inner cylinder 32 of top body 30a. The distal end of the first spring 100 bears on an outer rim 71 provided at the distal end of the piston rod 70. On these figures and in this ready to use position of the device 1, the first spring is in a compressed condition. The radial rim 31 and the outer rim 71 act as second retaining means for maintaining the first spring 100 in its compressed condition.

On these figures, the distal end of the second spring 110 bears on the proximal face of a radial rim 42 provided on the inner wall of the safety shield 40, and the proximal end of the second spring 110 bears on an inner abutment surface 63 (see FIG. 9) located on the ring 60. In the before use position of the device 1, the spring 110 is in a partially compressed condition.

On FIGS. 2 and 3, the flexible legs 33 of the inner cylinder 32 of the top body 30a are engaged in the abutment rim 72 of the piston rod 70.

As can be seen on FIGS. 4 and 5, in the ready to use position of the device 1, the distal leg 81 of the push button 80 faces the proximal projection 58 of the intermediate sleeve 50 which is on this figure in a first position. In consequence, if a user wishes to trigger the device by pushing on the push button 80, the distal movement of the push button 80 is restricted by way of leg 81 coming in abutment against the proximal projection 58. The push button 80 is therefore in a passive state, in which application of a distal force on the push button 80 does not cause the release of the second retaining means (31, 71).

Once the user is ready to use the device 1 of the invention, he removes the deshielder 90 as shown on FIG. 6. By removing the deshielder 90, he also removes the needle shield 21 and the device 1 is ready to be used. As appears from FIG. 6, after removing of the deshielder 90, the distal end of the safety shield 40 protrudes out of the bottom body 30b of the housing.

In order to proceed with the injection, the user grabs the device 1 by the housing 30 and he applies the distal end of the device 1, namely the distal end of the safety shield 40 on the site of injection (not shown). He then applies a distal force on the housing 30, which causes the safety shield 40 to move in the proximal direction with respect to the housing 30, due to the fact that the safety shield 40, which coupled to the housing 30 via the second spring 110, is movable with respect to the housing 30. The intermediate sleeve 50 being coupled to the housing 30, the proximal movement of the safety shield 40 has the consequence to cause the movement of the peg 41 in the proximal portion 56a of the cam 56 of the intermediate sleeve 50 as shown on FIG. 7. The movement of the peg 41 in the inclined proximal portion 56a of the cam 56 causes the intermediate sleeve 50 to rotate around said longitudinal axis A with respect to the safety shield 40, to the push button 80 and with respect to the ring 60. As shown on FIG. 8, this rotation around said longitudinal axis A of the intermediate sleeve 50 with respect to the ring 60 from its first position to a second position causes the radial stop 61 of the ring 60 to disengage from the abutment surface 52. The intermediate sleeve 50 acts as first deactivating means of the first retaining means.

Due to the advantageous design of the present invention, a user need only use minimal force when applying the device 1 against his or her skin. To cause the safety shield 40 to move in the proximal direction and place the container 20 in the active state, the user applies the device 1 against his or her skin, and with a low force, causes the safety shield 40 to move in the proximal direction. The container 20 is thus placed in the active state and the device 1 is ready for use.

In consequence, the container 20 is now in its active state. In this position, as shown on FIG. 7, the distal leg 81 of the push button 80 has rotated around said longitudinal axis A with respect to the intermediate sleeve 50 but it still faces the proximal projection 58 of the intermediate sleeve 50. Distal movement of the push button 80 is therefore still restricted by the distal leg 81 coming in abutment against the proximal projection 58 of the intermediate sleeve 50 and the push button 80, in other words the triggering means, is therefore still in its passive state. The distal leg 81 and the proximal projection 58 act as third retaining means for maintaining the triggering means in its passive state. The intermediate sleeve 50 is in a blocked position with respect to the distal leg 81.

The user then continues to apply a small distal force on the housing 30 and in the same way as described above, this causes the peg 41 to further move within the proximal portion 56a of the cam 56 of the intermediate sleeve 50 as shown on FIG. 11. This further movement of the peg 41 within the proximal portion 56a of the cam 56 causes further rotation around said longitudinal axis A of the intermediate sleeve 50 with respect to the push button 80. As shown on FIG. 11, the distal leg 81 of the push button 80 now faces the recess 57 located at the proximal end of the intermediate sleeve 50. In consequence, the distal movement of the push button 80 is now allowed and the push button 80 is now in its active state. The intermediate sleeve 50 has now reached a free position with respect to the distal leg 81. The intermediate sleeve 50 and the recess 57 act as second deactivating means of the third deactivating means. However, even if a user applies pressure to the push button 80 before placing the device 1 at the injection site, it is possible to activate the device 1 and effect an injection. The push button 80 is not locked in place nor prevented from being activated by the sequence of steps a user follows when using the device 1.

In the steps described above, the proximal portion 56a of the cam 56 acts as guiding means for the rotation of the intermediate sleeve 50 with respect to the safety shield 40. During these steps, the second spring 110 has been slightly compressed with respect to its initial condition.

The FIGS. 9-12 show the injection device 1 with both the container 20 and the push button 80 in their respective active state.

The force needed by the user in order to apply the device 1 on the injection site and in order to move safety shield 40 with respect to the housing 30 as described above is very low, in particular because the various deactivation of the retaining means is obtained by rotation around said longitudinal axis A of the intermediate sleeve 50 with respect to the safety shield 40. The device 1 is therefore very simple to use for the user.

Nevertheless, if the user misuses the device 1 by withdrawing it from the injection site at this moment, before triggering the injection by applying a force on the push button 80, the intermediate sleeve 50 simply rotates around said longitudinal axis A back under the action of the second spring 110 tending to come back to its initial condition and the device 1 is put back in its initial position as shown on FIGS. 4-6. As a consequence, the first deactivating means, ie the intermediate sleeve 50 in the example shown, is capable of rotating back around said longitudinal axis A from its second position to its first position, said rotation being caused by movement of said safety shield from its second position to its first position prior to activation of the triggering means.

With reference to FIGS. 13 and 14, the injection step as such may now be triggered by pushing distally on the push button 80.

With reference to FIGS. 13 and 14, by pushing distally on the push button 80, the inner legs 82 of the push button 80 deflect the flexible legs 33 of the top body 30a and therefore free the spring 100 which extends in the distal direction in view of returning to an uncompressed condition. By extending, the spring 100 draws with him the container 20 which, because it is in its active state, is allowed to move distally, thereby causing the penetration of the needle 3 in the injection site. As shown on FIGS. 15 and 16, the needle 3 now extends beyond the distal end of the housing 30 and of the safety shield 40 and the proper injection of the product 2 can take place.

Another case of misuse by the user is the following one: after having done the necessary as described above in order to put both the container 20 and the push button 80 in their respective active state as shown on FIGS. 11-14, the user may begin to push distally on the push button 80 and almost simultaneously he withdraws the device 1 from the injection site, for example on a distance of 1 mm. Usually, the user will not even notice he has withdrawn the device from the injection site and he will carry on applying a force on the push button. In devices of the prior art, in such a case, the push button is allowed to move distally, the spring is freed as described above and the injection is completed although not at the right insertion depth. In some devices of prior art comprising a ring such as the one described above, such ring may then prevent the container to move distally: in such a case, the needle is not allowed to penetrate the injection site, yet the spring is freed and the product is expelled out of the injection site, for example on the skin of the user.

The device 1 of the present invention shown on FIGS. 1-22 remedies this problem. When the container 20 and the push button 80 of the device 1 of the invention are in their respective active state as shown on FIGS. 11 and 12, if the user begins to push distally on the push button 80, and then withdraws the device 1 from the injection site for about 1 mm, then the safety shield 40 is not allowed to rotate back around said longitudinal axis A because of the distal leg 81 of the push button 80 coming in abutment against the lateral wall 58a of the proximal projection 58, and thereby forming a rotational stop for the rotation around said longitudinal axis A of the safety shield 40 with respect to the intermediate sleeve 50. In consequence, the safety shield 40 will only be able to move back distally with respect to the intermediate sleeve 50 under the action of the second spring 110 tending to come back to its initial condition, but only on a limited distance, corresponding the distance between the location of the peg 41 on FIG. 11 and the elbow 56d of the cam 56 formed by the junction of the proximal portion 56a and the intermediate portion 56c of the cam 56. The elbow 56d acts as first arresting means for maintaining the safety shield 40 in such a third position, wherein the peg 41 is in abutment on the elbow 56d. In such a configuration, as can been easily understood from FIGS. 11 and 12, the ring 60 remains disengaged from the abutment surface 52 of the window 51 of the intermediate sleeve 50. In consequence, because the ring 60 remains disengaged from the abutment surface 52, when the user continues applying a distal force on the push button 80, the container 20 is allowed to move distally: the penetration of the injection site by the needle 3 takes place and the injection can be completed in a correct way, although the user has misused the device 1 in the first place.

With reference to FIGS. 17 and 18, the injection is completed by virtue of spring 100 acting as a first biasing means on the piston rod 70 and causing the distal movement of the piston rod 70, thereby causing the product to be expelled via the needle 3. On FIGS. 17 and 18, the spring 100 is in its expanded state, the piston 4 has reached the distal end of the container 20 and all the product has been expelled.

During the insertion and injection steps as described above, the second spring 110 has been compressed, as shown on FIGS. 17 and 18, due to the distal movement of the container 20. During this movement, the ring 60, together with the container 50, has moved distally with respect to the intermediate sleeve 50 and its radial stop 61 has moved within the intermediate region 51c of the window 51 guided by the inclined slope 54 of the window 51, as shown on FIG. 16. As explained above, this distal and rotational movement of the ring 60 within the intermediate region of the window 51 has been possible regardless from the fact that the user has used the device correctly or not in the first place. In consequence, as shown on FIG. 15, the peg 41 has rotated around said longitudinal axis A with respect to the intermediate sleeve 50 and it is now at the proximal end of the intermediate portion 56c of the cam 56. As is clear from FIG. 15, the intermediate portion 56c of the cam 56 is longitudinal.

In consequence, at the end of the injection, because of the peg 41 being now in regards with the longitudinal intermediate portion 56c of the cam 56, the withdrawal of the device 1 from the injection site causes the distal movement of the safety shield 40 drawn by the second spring 110 tending to come back to an extended condition and hereby acting as a second biasing means for biasing the safety shield 40 from its third position to a fourth position, as shown on FIG. 19. As shown on FIGS. 19-22, the safety shield 40 now covers the needle 3 and the injection device 1 can be safely handed. As can be seen on FIG. 21, during the distal movement of the safety shield 40, the peg 41 has moved distally within the intermediate portion 56c of the cam 56 of the intermediate sleeve 50. The cam 56 therefore acts as guiding means for the distal movement of the safety shield 40.

As shown on FIG. 21, the safety shield is now locked in its extended position by means of peg 41 blocked in the distal portion 56b of the cam 56 of the intermediate sleeve 50. Indeed, during the distal movement of the peg 41 within the longitudinal intermediate portion 56c of cam 56, the peg has been able to overcome the flexible tab 59. Once the peg 41 has reached the very distal end of the intermediate portion 56c, the flexible tab 59 now acts as a stop and prevents the proximal movement of the peg 41 in said intermediate portion 56c. The safety shield 40 is therefore prevented to move back to a retracted position and the device 1 is totally safe and can be disposed of.

With reference to FIGS. 23 and 24 is shown a variant of the device 1 of the invention, in which the housing 30 is capable of rotating around the longitudinal axis A of the device with respect to the intermediate sleeve 50. The references designating the same elements as in the device of FIGS. 1-22 have been maintained.

On FIG. 23 are shown partially the housing 30, the safety shield 40 and the intermediate sleeve 50. As can be seen on this figure, in this variant of the device of the invention, a peg 151 is provided on the inner wall of the intermediate sleeve 50 and a cam 141 is provided in the wall of the safety shield 40. The peg 151 and the cam 141 cooperate in the same manner as described for the peg 41 and the cam 56 of the device 1 of FIGS. 1-22 in order to rotate the safety shield 40 around the longitudinal axis A with respect to the intermediate sleeve 50 when the user applies a distal force on the housing of the device once he has applied the distal end of the device on the injection site.

The embodiment of the device of the invention of FIGS. 23 and 24 also comprises a flexible tab 152, provided in a window 153 cut in the wall of the intermediate sleeve 50 and able to be deflected tangentially. The flexible tab 152 is also provided with an outer radial protrusion 154 which is engaged in a window 130 arranged in the wall of the housing 30 (see FIG. 23). In the initial position of the device, the tab 152 is in its rest or non deflected position as shown on FIG. 24. Once the user has performed the steps necessary to put the push button and the container in their respective active state, as explained for the device 1 of FIGS. 1-22, the intermediate sleeve 50 has rotated around said longitudinal axis A with respect to the safety shield 40 and also with respect to the housing 30. The outer radial protrusion 154 engaged in the window 130 of the housing 30 has followed the rotation around said longitudinal axis A of the window 130 together with the rotation around said longitudinal axis A of the housing 30 with respect to the intermediate sleeve 50 and has therefore caused the flexible tab 152 to deflect.

Therefore, after the user has exerted a distal force on the housing 30 of the device in order to put the container and the push button in their active state, if the user at this time decides to withdraw the device from the injection site before triggering the injection by pushing distally the push button, then the device is put back in its initial position by virtue of both the second spring (as explained for the device of FIGS. 1-22) and the flexible tab 152 tending to come back to their initial position: under the combined action of the second spring and the flexible tab 152 tending to come back to their initial condition, the intermediate sleeve 50 rotates back around said longitudinal axis A to its initial position.

With reference to FIG. 24, the distal leg 81 of the push button 80 is provided with a plurality of teeth 181 and the lateral wall of the proximal projection 58 is provided with a plurality of grooves 158. These teeth 181 and grooves 158 are intended to cooperate together in the case the user withdraws the device from the injection site after having triggered the push button 80 and before the container has reached its insertion position. Indeed, in such a case, the user has performed the necessary steps as described above in order to put both the container and the push button in their respective active state: the distal leg 81 of the push button therefore faces the recess 57 of the intermediate sleeve 50. The user begins to push distally the push button 80 and, before the container has reached its insertion state, he releases the pressure he exerts on the housing and withdraws, for example on a distance of 1 mm, the device from the injection site: by way of the second spring and the flexible tab 152 tending to come back to their initial position, the intermediate sleeve 50 rotates back around said longitudinal axis A with respect to the push button 80 and the teeth 181 of the distal leg 81 engage the grooves 158 of the lateral wall 58 of the intermediate sleeve 50, thereby blocking further distal movement of the push button 80 and preventing an incorrect injection step. In order to proceed with the injection, the user only needs to put the distal end of the device back on the injection site and to exert again a distal force on the housing: the intermediate sleeve 50 then rotates around said longitudinal axis A once again with respect to the safety shield 40 in the correct way and the teeth 181 disengage from the grooves 158, thereby allowing the user to continue to push distally on the push button 80 in order to complete a safe and correct injection step.

The device of the invention only requires a low force to be applied by the user on the housing at the time of injection. For example the needed force may be inferior to 5 Newton. Moreover, the device of the invention reduces the risk of potential mis-use by the user. In particular, in case the user mis-uses the device of the invention, then the product is not lost and the injection may be correctly and safely completed in the end.

The invention claimed is:

1. A device for automatic injection of a product into an injection site, said device having a longitudinal axis A and comprising:

a housing capable of receiving a container, said container being provided at one distal end with a needle and being movable relative to said housing between an initial position in which a distal end of said needle does not extend beyond a distal end of said housing and in which the container is in one of a passive state and an active state, to an insertion position, distally spaced relative to said initial position, in which said distal end of said needle extends beyond said distal end of said housing, movement of the container out of its initial position being prevented when the container is in its passive state, and being permitted when the container is in its active state, and a safety shield coupled to and movable with respect to said housing between a first position and a second position, proximally spaced with respect to said first position, said safety shield having a free end that is distally spaced beyond a distal end of the needle when said safety shield is on said second position, movement of said safety shield from its first position to its second position placing the container in its active state, first retaining means for maintaining the container in its passive state, first deactivating means, capable of rotating with respect to said first retaining means around said longitudinal axis A from a first position, in which said first retaining means maintain the container in its passive state, to a second position, in which said first retaining means are deactivated and allow the passage of the container in its active state, rotation around said longitudinal axis A of said first deactivating means from its first position to its second position being caused by movement of said safety shield from its first position to its second position under distal pressure exerted on said housing, first biasing means coupled to said housing for biasing the container toward said insertion position, said first biasing means being in one of a compressed condition, in which the container is in its initial position, and an extended condition, in which the container is in its insertion position, and second retaining means for maintaining said first biasing means in its compressed condition, triggering means being activatable by application of a force on said triggering means to release said second retaining means, said triggering means being in one of a passive state, in which application of said force on said triggering means cannot cause the release of said second retaining means, and an active state in which application of said force on said triggering means causes the release of said second retaining means, wherein movement of said safety shield from its first position to its second position causes passage of said triggering means from its passive state to its active state.

2. Device according to claim 1, wherein it further comprises:
third retaining means for maintaining said triggering means in its passive state,
second deactivating means, capable of rotating with respect to said third retaining means around said longitudinal axis A from a blocked position, in which said third retaining means maintain said triggering means in its passive state, to a free position, in which said third retaining means allow the passage of said triggering means in its active state, rotation around said longitudinal axis A of said second deactivating means from its blocked position to its free position being caused by movement of said safety shield from its first position to its second position.

3. Device according to claim 2, wherein part of said first and second deactivating means are formed on at least one intermediate sleeve received within said housing, said intermediate sleeve being movable in rotation around said longitudinal axis A from a first position to a second position in response to movement of said safety shield at least out of its first position.

4. Device according to claim 3, wherein
said first retaining means comprising at least a ring received within said safety shield and coupled to said container, said ring comprising at least an outer radial stop,
said first deactivating means comprises a window arranged in said intermediate sleeve, said window comprising an abutment surface,
said radial stop being engaged on said abutment surface in the first position of said intermediate sleeve, and being disengaged from said abutment surface after rotation of said intermediate sleeve around said longitudinal axis A.

5. Device according to claim 3, wherein:
said third retaining means comprising at least a distal leg located on said triggering means in regard of the proximal end of said intermediate sleeve,
said second deactivating means comprise a proximal recess arranged at the proximal end of said intermediate sleeve,
said distal leg being in spaced relation to the proximal end of said intermediate sleeve in the first position of said intermediate sleeve, and being in regard with said recess after rotation around said longitudinal axis A of the intermediate sleeve, thereby allowing distal movement of said triggering means by application of a force exerted on said triggering means.

6. Device according to claim 5, wherein it further comprises guiding means designed for causing the rotation around said longitudinal axis A of said intermediate sleeve with respect to said safety shield when distal pressure is exerted on said housing.

7. Device according to claim 6, wherein said guiding means include at least a peg located on said intermediate sleeve or on said safety shield and a first cam located respectively on said safety shield or on said intermediate sleeve and in which said peg is engaged so as to be able to move slidingly and reversibly within said first cam, said first cam being inclined with respect to the longitudinal axis A of said device, the movement of said peg within said first cam when distal pressure is applied on said housing causing rotation of said intermediate sleeve around said longitudinal axis A.

8. Device according to claim 5, wherein it comprises first return means designed for biasing said safety shield from its second position to its first position when distal pressure exerted on said housing is released before activation of said triggering means, said guiding means causing the intermediate sleeve to rotate back in its first position around said longitudinal axis A.

9. Device according to claim 8, wherein said first return means comprise at least a spring, said spring being in a compressed condition when said safety shield is in its second position.

10. Device according to claim 8, wherein said first return means further comprise a flexible tab located on said intermediate sleeve, said flexible tab being in a rest position when said intermediate sleeve is in its first position and being in a tangentially deflected position when said intermediate sleeve is in its second position, said intermediate sleeve being movable in rotation around said longitudinal axis A with respect to said housing, said flexible tab having a radial protrusion engaged in a window located on said housing, said flexible tab aiming at coming back to its rest position when distal pressure exerted on said housing is released, thereby causing said intermediate sleeve to rotate back to its first position around said longitudinal axis A.

11. Device according to claim 5, wherein it further comprises locking means designed for preventing the intermediate sleeve to rotate back around said longitudinal axis A to its first position when distal pressure exerted on said housing is released after activation of said triggering means but before the container reaches its insertion position, said locking means comprising a lateral wall of said recess, said distal leg being at least in abutment on said lateral wall after activation of said triggering means, thereby preventing the rotation around said longitudinal axis A of said intermediate sleeve with respect to said triggering means.

12. Device according to claim 11, wherein said distal leg comprises at least one tooth and said lateral wall comprises at least one groove, said at least one tooth being caused to engage said at least one groove if distal pressure exerted on said housing is released after activation of said triggering means and before the container reaches its insertion position, so that further activation of said triggering means is prevented.

13. Device according to claim 11, wherein:
said safety shield being movable with respect to the container to a third position, in which the tip of the needle extends beyond a distal end of said safety shield, and to a fourth position, in which the tip of the needle does not extend beyond a distal end of said safety shield,
said device further comprises
second biasing means coupled to said safety shield for biasing said safety shield from its third position to its fourth position when distal pressure exerted on said housing is released,
first arresting means designed for maintaining said safety shield substantially in its third position, if distal pressure exerted on said housing is released after activation of said triggering means and before the container reaches its insertion position,
third deactivating means designed for deactivating said first arresting means when the container is in its insertion position.

14. Device according to claim 13, wherein said first arresting means comprise an abutment surface formed in said first cam, said peg coming in abutment on said abutment surface and thereby preventing further movement of said safety shield with respect to said intermediate sleeve when distal pressure exerted on said housing is released after activation of said triggering means and before the container reaches its insertion position.

15. Device according to claim 14, wherein said first retaining means comprising at least a ring received within said safety shield and coupled to said container, said ring comprising at least an outer radial stop, said ring being coupled to the container, said first deactivating means comprises a window arranged in said intermediate sleeve, said window comprising an abutment surface, said radial stop being engaged on said abutment surface in the first position of said intermediate sleeve, and being disengaged from said abutment surface after rotation of said intermediate sleeve around said longitudinal axis A, and wherein said third deactivating means comprise an inclined slope located in said window, said radial stop of said ring cooperating with said slope so as to cause a further rotation around said longitudinal axis A of said intermediate sleeve with respect to said safety shield, when the container moves from its initial position to its insertion position, thereby causing said peg to disengage from said abutment surface and to engage the proximal end of a second cam formed on said intermediate sleeve or on said safety shield, said second cam extending longitudinally in the distal direction.

16. Device according to claim 15, wherein it further comprises second arresting means for preventing the movement of said safety shield from its fourth position to its third position.

17. Device according to claim 16, wherein said second arresting means comprise a flexible tab located in the distal region of said second cam, said flexible tab being able to be overcome by said peg during the movement of said safety shield from its third position to its fourth position, said flexible tab forming a stop with respect to the proximal movement of said peg when said safety shield is in its fourth position.

18. Device according to claim 1, wherein said first deactivating means is capable of rotating around said longitudinal axis A from its second position to its first position, said rotation being caused by movement of said safety shield from its second position to its first position prior to activation of the triggering means.

* * * * *

UNITED STATES PATENT AND TRADEMARK OFFICE
CERTIFICATE OF CORRECTION

PATENT NO. : 8,568,359 B2
APPLICATION NO. : 12/679706
DATED : October 29, 2013
INVENTOR(S) : Carrel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 696 days.

Signed and Sealed this

Fifteenth Day of September, 2015

Michelle K. Lee
*Director of the United States Patent and Trademark Office*